(12) United States Patent
Wilmer et al.

(10) Patent No.: US 8,263,789 B2
(45) Date of Patent: Sep. 11, 2012

(54) CATALYST SYSTEM AND METHOD FOR GAS PHASE OXIDATION USING AN UPSTREAM LAYER

(75) Inventors: Hagen Wilmer, Ludwigshafen (DE); Jürgen Zühlke, Speyer (DE); Thomas Lautensack, Birkenau (DE); Hans-Martin Allmann, Neunkirchen (DE); Frank Rosowski, Mannheim (DE); Cornelia Dobner, Ludwigshafen (DE)

(73) Assignee: BASF SE (DE)

( * ) Notice: Subject to any disclaimer, the term of this patent is extended or adjusted under 35 U.S.C. 154(b) by 492 days.

(21) Appl. No.: 12/520,648

(22) PCT Filed: Dec. 12, 2007

(86) PCT No.: PCT/EP2007/063810
§ 371 (c)(1),
(2), (4) Date: Jun. 22, 2009

(87) PCT Pub. No.: WO2008/077791
PCT Pub. Date: Jul. 3, 2008

(65) Prior Publication Data
US 2010/0029955 A1    Feb. 4, 2010

(30) Foreign Application Priority Data
Dec. 21, 2006  (EP) .................................... 06126893

(51) Int. Cl.
*C07D 307/89*    (2006.01)

(52) U.S. Cl. ........................ 549/248; 549/249

(58) Field of Classification Search ............... 549/248, 549/249
See application file for complete search history.

(56) References Cited

U.S. PATENT DOCUMENTS

| | | | |
|---|---|---|---|
| 5,225,574 A | 7/1993 | Aichinger et al. | |
| 6,624,114 B1 | 9/2003 | Eberle et al. | |
| 6,700,000 B1 | 3/2004 | Heidemann et al. | |
| 7,338,918 B2 | 3/2008 | Neto et al. | |
| 7,371,893 B2 | 5/2008 | Storck et al. | |
| 7,390,911 B2 | 6/2008 | Neto et al. | |
| 7,615,513 B2* | 11/2009 | Guckel et al. | 502/350 |
| 7,687,425 B2* | 3/2010 | Storck et al. | 502/102 |
| 2006/0276661 A1 | 12/2006 | Storck et al. | |
| 2008/0064593 A1 | 3/2008 | Guckel et al. | |
| 2008/0154048 A1 | 6/2008 | Guckel et al. | |
| 2008/0194844 A1 | 8/2008 | Guckel et al. | |

FOREIGN PATENT DOCUMENTS

| | | |
|---|---|---|
| DE | 4013051 A1 | 11/1991 |
| DE | 19823262 A1 | 12/1999 |
| DE | 1108470 A1 | 6/2001 |
| DE | 1032817 A1 | 12/2004 |

(Continued)

OTHER PUBLICATIONS

U.S. Appl. No. 12/015,741, filed Jan. 17, 2008, Raichle et al.

(Continued)

*Primary Examiner* — Taylor Victor Oh
(74) *Attorney, Agent, or Firm* — Connolly Bove Lodge & Hutz LLP

(57) ABSTRACT

The present invention relates to a process for gas-phase oxidation, in which a gaseous stream comprising an aromatic hydrocarbon and molecular oxygen is passed through two or more catalyst zones. Furthermore, the present invention relates to a catalyst system for gas-phase reaction using a preliminary zone.

23 Claims, 1 Drawing Sheet

FOREIGN PATENT DOCUMENTS

Figure 1A:
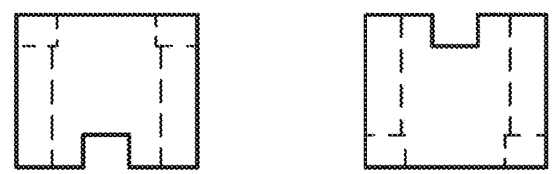
Figure 1A:
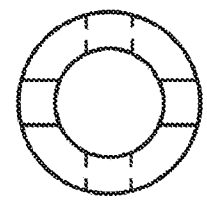

| | | |
|---|---|---|
| DE | 10323461 A1 | 12/2004 |
| DE | 10323818 A1 | 12/2004 |
| DE | 102004014918 A1 | 10/2005 |
| EP | 1063222 A1 | 12/2000 |
| EP | 10484 115 | 3/2001 |
| EP | 1108470 | 6/2001 |
| EP | 1452227 A1 | 9/2004 |
| GB | 721412 | 1/1955 |
| GB | WO-99/61433 A1 | 12/1999 |
| WO | WO-2004/103561 A1 | 12/2004 |
| WO | WO-2005/115616 A1 | 12/2005 |
| WO | WO-2006/092304 A1 | 9/2006 |
| WO | WO-2006/092305 A1 | 9/2006 |
| WO | WO-2007/116018 A1 | 10/2007 |
| WO | WO-2008/022909 | 2/2008 |
| WO | WO-2008/022911 | 2/2008 |
| WO | WO-2009/021924 | 2/2009 |
| WO | WO-2009/124947 | 10/2009 |

OTHER PUBLICATIONS

U.S. Appl. No. 12/039,231, filed Feb. 28, 2008, Cremer et al.
U.S. Appl. No. 12/138,823, filed Jun. 13, 2008, Raichle et al.
U.S. Appl. No. 12/138,862, filed Jun. 13, 2008, Cremer et al.
U.S. Appl. No. 12/297,895, filed Oct. 21, 2008, Maurer et al.
U.S. Appl. No. 12/298,453, filed Oct. 24, 2008, Lautensack et al.
U.S. Appl. No. 12/301,370, filed Nov. 18, 2008, Mackewitz et al.
U.S. Appl. No. 12/301,352, filed Nov. 18, 2008, Mackewitz et al.
U.S. Appl. No. 12/301,420, filed Nov. 18, 2008, Wilmer et al.
U.S. Appl. No. 12/305,698, filed Dec. 19, 2008, Wilmer et al.
U.S. Appl. No. 12/936,807, filed Oct. 7, 2010, Wilmer et al.

* cited by examiner

CATALYST SYSTEM AND METHOD FOR GAS PHASE OXIDATION USING AN UPSTREAM LAYER

CROSS-REFERENCE TO RELATED APPLICATIONS

This application is a national stage application (under 35 U.S.C. §371) of PCT/EP2007/063810, filed Dec. 12, 2007, which claims benefit of European application 06126893.4, filed Dec. 21, 2006.

BACKGROUND OF THE INVENTION

The present invention relates to a process for gas-phase oxidation, in which a gaseous stream comprising an aromatic hydrocarbon and molecular oxygen is passed through two or more catalyst zones. Furthermore, the present invention relates to a catalyst system for gas-phase reaction using a preliminary zone.

Many carboxylic acids and/or carboxylic anhydrides are prepared industrially by catalytic gas-phase oxidation of aromatic hydrocarbons such as benzene, the xylenes, naphthalene, toluene or durene in fixed-bed reactors. In this way, it is possible to obtain, for example, benzoic acid, maleic anhydride, phthalic an hydride, isophthalic acid, terephthalic acid or pyromellitic anhydride. In general, a mixture of an oxygen-comprising gas and the starting material to be oxidized is passed through tubes in which a bed of a catalyst is present. To regulate the temperature, the tubes are surrounded by a heat transfer medium, for example a salt melt.

Although the excess heat of reaction is removed by the heat transfer medium, local temperature maxima (hot spots) in which the temperature is higher than in the remainder of the catalyst bed can be formed in the catalyst bed. These hot spots lead to secondary reactions, e.g. total combustion of the starting material, or to formation of undesirable by-products which cannot be separated, or separated only with great difficulty, from the reaction product.

In addition, the catalyst can be irreversibly damaged above a particular hot spot temperature. For this reason, the loading of the gaseous stream with the hydrocarbon to be oxidized has to be kept very low at the beginning when starting up the process and can be increased only slowly. The final production state is often reached only after a few weeks.

In recent years, multizone catalyst systems have been used for the oxidation of aromatic hydrocarbons (for example DE-A 40 13 051, DE-A 198 23 262, EP-A 1 063 222, WO 2005/115616, EP-A 1 084 115, DE-A 103 23 818, DE-A 103 23 461, DE-A 103 23 817). The objective is to match the activity of the individual catalyst zones to the reaction profile along the axis of the reactor. This makes it possible to achieve a high yield of desired product and at the same time a very low yield of the undesirable intermediates or by-products. The catalysts of the first zone closest to the reactor inlet usually have the lowest activity since the highest starting material concentration and thus the greatest reaction rate occur in the region close to the reactor inlet. The heat liberated in the chemical reaction heats the reaction gas up to the point at which the energy produced by the reaction is the same as the energy given off to the coolant. An excessively high activity in the first catalyst zone would lead to an uncontrolled increase in the hot spot temperature, which can usually lead to a reduction in selectivity or even to the reaction becoming uncontrollable.

A further aspect which has to be taken into account in configuring the activity of the individual catalyst zones is the position of the hot spot in the first catalyst zone. Since the catalyst activity decreases with increasing time of operation, a higher proportion of unreacted hydrocarbons or partially oxidized intermediates gets into regions of the catalyst bed located further downstream. The reaction thus moves further toward the reactor outlet and the position of the hot spot shifts ever further in the direction of the reactor outlet. This can even lead to the hot spot migrating from the first catalyst zone into the second or a subsequent catalyst zone. This migration of the hot spot results in a significant decrease in the yield of desired product.

The deactivation of the catalyst can be countered to a limited extent by increasing the temperature of the heat transfer medium. The increase in the temperature of the heat transfer medium and/or the movement of the hot spot lead, in the case of multizone catalyst systems, to the temperature at which the gas mixture enters a subsequent catalyst zone increasing. Since downstream catalyst zones are generally more active but less selective, undesirable overoxidation and other secondary reactions increase. These two effects result in the product yield or selectivity decreasing with increasing time of operation. In such a case, a complete replacement of the catalyst can be more economically advantageous than continuation of operation.

A disadvantage of the activity-structured catalyst systems reported in the prior art is that, despite the use of such structured catalyst systems, the life of the catalysts is not satisfactory, in particular in respect of the continual movement of the hot spot in the direction of the gas stream. A positioning of the hot spot in a more active catalyst zone further toward the gas outlet also restricts the opportunity of making a fine adjustment in the selectivity of the catalyst to avoid undesirable by-products.

WO 2006/92305, WO 2006/92304 and the European patent application number 06112510.0 solve this problem by the use of an active catalyst zone which is located upstream of the usual catalyst zones toward the gas outlet. This active preliminary zone effects more rapid heating of the reactor gases and thus an earlier start of the chemical reaction, so that the hot spot forms further toward the gas outlet compared to the systems of the prior art.

However, a disadvantage of a more active preliminary zone is that a further suspension of active compositions for the preliminary zone has to be prepared in addition to the suspensions of active compositions for the subsequent three to four catalyst zones. Furthermore, a very active first zone at the reactor inlet represents an increased safety risk since the reaction can become uncontrollable because of the high proportion of starting material at the reactor inlet.

A further disadvantage of the prior art is that the gas temperature at the reactor inlet is far below the salt bath temperature. In this region, the salt bath serves not to remove excess heat but instead to heat the reaction gas. An unfilled, empty tube, a tube filled with inert spherical material or a tube filled with catalyst is usually used for heating the reaction gas. The disadvantage of inert spherical material is the high pressure drop over the reactor.

BRIEF SUMMARY OF THE INVENTION

The invention relates to a process for gas-phase oxidation which comprises passing a gaseous stream comprising at least one aromatic hydrocarbon and molecular oxygen through at least two catalyst zones arranged in series in the flow direction of the gaseous stream and the activities of the catalysts in adjoining catalyst zones are different from one another, wherein a catalyst and/or inert zone precedes the adjoining catalyst zones in a direction opposite to the flow direction of the gas, with the product of diameter times height of the preceding inert or catalyst rings being smaller than at least one of the subsequent catalyst zones or the volume of the preceding inert or catalyst rings being smaller than at least one of the subsequent catalyst zones or the ratio of surface area to volume of the preceding inert or catalyst rings being greater than at least one of the subsequent catalyst zones.

It was therefore an object of the present invention to provide a process for the gas-oxidation of aromatic hydrocarbons and a catalyst system for carrying out this process, in which the heating of the reaction gases at the reactor inlet occurs more quickly than in the prior art or in which the heating of the reaction gases at the reactor inlet occurs in a comparable time as when using the invention of WO 2006/92305, WO 2006/92304 or the European patent application number 06112510.0, but the achievement of this more rapid heating is simpler to carry out and does not bring with it an increased safety risk. More rapid heating enables a more rapid commencement of the reaction to be achieved, with the hot spot being formed further toward the gas inlet. A further object was to provide a catalyst system whose hot spot is formed closer toward the gas inlet than in the prior art. Consequently, catalyst systems which achieve a longer operating life at a high yield level are to be provided.

DETAILED DESCRIPTION OF THE INVENTION

The object is achieved by a process for gas-phase oxidation, in which a gaseous stream comprising at least one aromatic hydrocarbon and molecular oxygen is passed through at least two catalyst zones arranged in series in the flow direction of the gaseous stream and the activities of the catalysts in adjoining catalyst zones are different from one another, wherein a catalyst and/or inert zone precedes the adjoining catalyst zones in a direction opposite to the flow direction of the gas, with the product of diameter times height of the preceding inert and/or catalyst rings being smaller than at least one of the subsequent catalyst zones or the volume of the preceding inert and/or catalyst rings being smaller than at least one of the subsequent catalyst zones or the ratio of surface area to volume of the preceding inert and/or catalyst rings being greater than at least one of the subsequent catalyst zones.

The preceding catalyst and/or inert zone accordingly represents the first zone (toward the gas inlet) of the catalyst system.

It is also possible to use mixtures of various inert and/or catalyst rings in the preliminary zone. The data given for the preceding inert and/or catalyst rings are then in each case based on the average product, the average volume or the average ratio.

The product of diameter times height of the preceding inert and/or catalyst rings is advantageously smaller than that of at least two, preferably at least three, in particular all, of the subsequent catalyst zones.

For the purposes of the present invention, the term "diameter" refers to the average external diameter of the preceding inert and/or catalyst rings.

For the purposes of the present invention, the term "volume" refers to the geometric volume of the ring.

The volume of the preceding inert and/or catalyst rings is advantageously less than that of at least two, preferably at least three, in particular all, of the subsequent catalyst zones.

Figure 1B:
Figure 1B:
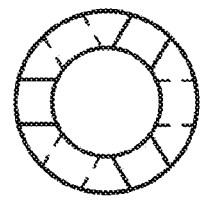

The volume of the preceding catalyst rings can, for example, be reduced by notches or slits which extend over the complete catalyst ring. The volume is particularly preferably reduced by several notches on the upper side and several notches on the underside of the rings (on each end face). The volume is very particularly preferably reduced by two, three, four or five symmetrically located notches on the upper side and two, three, four or five symmetrically located notches on the underside of the rings (on each end face). The volume is further very particularly preferably reduced by two symmetrical notches on the upper side and two symmetrical notches on the underside of the rings (on each end face), with the notches on the upper side and those on the underside being identical but rotated by 90°. These notches are shown in FIG. 1a. The volume is further very particularly preferably reduced by three symmetrical notches on the upper side and three symmetrical notches on the underside of the rings (on each end face), with the notches on the upper side and those on the underside being identical. These notches are shown in FIG. 1b.

The ratio of surface area to volume of the preceding inert and/or catalyst rings is advantageously greater than that of at least two, preferably at least three, in particular all, of the subsequent catalyst zones.

The preceding inert and/or catalyst zone is advantageously followed by at least three further catalyst zones, preferably from 3 to 5 further catalyst zones.

For the present purposes, a catalyst zone is the bed of a catalyst having essentially uniform activity, i.e. with an essentially uniform make-up of the active composition, proportion of active composition and packing density (with the exception of unavoidable fluctuations in charging the reactor). Successive catalyst zones thus differ in the activity of the catalysts comprised. Various measures for controlling the catalyst activity are known to those skilled in the art.

The activity of the catalyst zones preferably increases continuously from the first catalyst zone after the preceding inert and/or catalyst zone through to the last catalyst zone (viewed in the flow direction). However, intermediate zones of catalysts having a low activity or of inert material can also be integrated into the system (see, for example, the European patent application number 06008816.8).

The product of diameter times height of the preceding inert or catalyst rings is advantageously at least 5-10% smaller than the product of diameter times height of at least one of the subsequent catalyst zones. The product is advantageously at least 10-20% smaller. The product of diameter times height of the preceding inert or catalyst rings is advantageously smaller than or equal to 45 mm$^2$, preferably smaller than or equal to 40 mm$^2$. The product of diameter times height of the preceding inert or catalyst rings is advantageously from 15 to 45 mm$^2$, preferably from 25 to 40 mm$^2$. The diameter of the preceding inert or catalyst rings is advantageously from 3 to 8 mm, preferably from 5 to 7 mm. The height of the preceding inert or catalyst rings is advantageously from 3 to 8 mm, preferably from 5 to 7 mm. The internal diameter of the preceding inert or catalyst rings is advantageously from 1 to 6 mm, preferably from 3 to 5 mm.

The volume of the preceding inert or catalyst rings is advantageously at least 5-10% smaller than the volume of at least one of the subsequent catalyst zones. The volume is advantageously at least 10-20% smaller. The volume of the preceding inert or catalyst rings is advantageously less than or equal to 170 mm$^3$, preferably less than or equal to 110 mm$^3$. The volume of the preceding inert or catalyst rings is advantageously from 25 to 170 mm$^3$, preferably from 60 to 110 mm$^3$.

The ratio of surface area to volume of the preceding inert or catalyst rings is advantageously at least 5-10% greater than the ratio of surface area to volume of at least one of the subsequent catalyst zones. The ratio of surface area to volume is advantageously at least 10-20% greater. The ratio of surface area to volume of the preceding inert or catalyst rings is advantageously greater than or equal to 180 mm$^{-1}$, preferably greater than or equal to 200 mm$^1$. The ratio of surface area to volume of the preceding inert or catalyst rings is advantageously from 180 to 500 mm$^{-1}$, preferably from 200 to 300 mm$^{-1}$.

The preceding inert and/or catalyst rings advantageously have an activity ranging from 0 to the activity of the first subsequent catalyst zone. The preceding inert and/or catalyst rings particularly preferably have either no activity or the activity of the first subsequent catalyst zone.

For the purposes of the present invention, the activity of a catalyst or a catalyst zone is the conversion under identical conditions (in particular in respect of catalyst volume, gas hourly space velocity (GHSV) or amount of air, temperature of the heat transfer medium, hydrocarbon loading of the gaseous stream) measured in a test plant. The higher the conversion of a catalyst or a catalyst zone, the higher its activity. This method is suitable, in particular, for comparison of activities or for determining relative catalyst activities.

The methods of controlling the activity of a catalyst zone are adequately known to those skilled in the art. For example, the activity/selectivity of the catalysts can be varied by addition of promoters to the active composition, by adjusting the BET surface area of the catalysts, by means of the proportion of active composition, i.e. the active composition per tube volume, by means of the empty space between the individual shaped catalyst bodies or by the content of inert materials.

In the case of an inactive preliminary zone, this comprises an inert material, for example as is also used as catalyst support. Suitable support materials are, for example, silica ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The inactive preliminary zone can also comprise woven meshes, drawn-loop knitted meshes or formed-loop knitted meshes made of fibers or metal wires.

The total length of all catalyst zones including the preliminary zone composed of inert and/or catalyst material is usually from 2.5 to 4 m, preferably from 2.8 to 3.4 m. The length of the preliminary zone is advantageously from 0.05 to 1 m, preferably from 0.1 to 0.5 m, in particular from 0.15 to 0.4 m. The bed length of the preceding inert and/or catalyst rings is therefore advantageously from 1.5 to 40% of the total bed length, preferably from 2.5 to 20%, in particular from 3.5 to 15%.

In a three-zone catalyst system having a preceding inert and/or catalyst zone, the inert and/or catalyst zone advantageously makes up from 1 to 40%, preferably from 5 to 25%, in particular from 10 to 20%, of the total length of the catalyst bed. The first subsequent catalyst zone advantageously makes up from 15 to 75%, preferably from 25 to 60%, in particular from 30 to 50%, of the total length of the catalyst bed. The second subsequent catalyst zone advantageously makes up from 5 to 45%, preferably from 10 to 40%, in particular from 15 to 30%, of the total length of the catalyst bed. The third subsequent catalyst zone likewise advantageously makes up from 5 to 45%, preferably from 10 to 40%, in particular from 15 to 30%, of the total length of the catalyst bed.

In a three-zone catalyst system having a preceding inert and/or catalyst zone, the bed length of the preceding catalyst zone is advantageously from 5 cm to 120 cm, preferably from 15 cm to 75 cm, in particular from 30 cm to 60 cm, the bed length of the first subsequent catalyst zone is advantageously from 45 cm to 225 cm, preferably from 75 cm to 180 cm, in particular from 90 cm to 150 cm, the bed length of the second subsequent catalyst zone is advantageously from 15 cm to 135 cm, preferably from 30 cm to 120 cm, in particular from 45 cm to 90 cm, and the bed length of the third subsequent catalyst zone is advantageously from 15 cm to 135 cm, preferably from 30 cm to 120 cm, in particular from 45 cm to 90 cm.

The catalytic make-up of a three-zone catalyst system is described, for example, in WO 2004/103561 on page 7.

In a four-zone catalyst system having a preceding inert and/or catalyst zone, the preceding inert and/or catalyst zone advantageously makes up from 1 to 40%, preferably from 5 to 25%, in particular from 10 to 20%, of the total length of the catalyst bed. The first subsequent catalyst zone advantageously makes up from 15 to 75%, preferably from 25 to 60%, in particular from 30 to 50%, of the total length of the catalyst bed. The second subsequent catalyst zone advantageously makes up from 5 to 45%, preferably from 5 to 30%, in particular from 10 to 20%, of the total length of the catalyst bed. The third subsequent catalyst zone advantageously makes up from 5 to 45%, preferably from 5 to 30%, in particular from 10 to 25%, of the total length of the catalyst bed. The fourth subsequent catalyst zone likewise advantageously makes up from 5 to 45%, preferably from 5 to 30%, in particular from 10 to 25%, of the total length of the catalyst bed.

In a four-zone catalyst system having a preceding inert and/or catalyst zone, the bed length of the preceding inert and/or catalyst zone is advantageously from 5 cm to 120 cm, preferably from 15 cm to 75 cm, in particular from 30 cm to 60 cm, the bed length of the first subsequent catalyst zone is advantageously from 45 cm to 225 cm, preferably from 75 cm to 180 cm, in particular from 90 cm to 150 cm, the bed length of the second subsequent catalyst zone is advantageously from 15 cm to 135 cm, preferably from 15 cm to 90 cm, in particular from 30 cm to 60 cm, the bed length of the third subsequent catalyst zone is advantageously from 15 cm to 135 cm, preferably from 15 cm to 90 cm, in particular from 30 cm to 75 cm, and the bed length of the fourth subsequent catalyst zone is advantageously from 15 cm to 135 cm, preferably from 15 cm to 90 cm, in particular from 30 cm to 75 cm.

The catalytic make-up of a four-zone catalyst system is described, for example, in WO 2004/103561 on page 8 or in the European patent application number 06114230.3 on pages 5 and 6.

It is preferred that no hot spots are formed in the preceding catalyst zone.

The preliminary zone is particularly preferably made up of two regions. The first region closest to the gas inlet comprises a bed of inert material while the second, downstream region (closest to the other catalyst zones) comprises a bed of catalyst material, with the product of diameter times height of the preceding inert and catalyst rings being smaller than at least one of the subsequent catalyst zones or the volume of the preceding inert and catalyst rings being smaller than at least one of the subsequent catalyst zones or the ratio of surface area to volume of the preceding inert and catalyst rings being greater than at least one of the subsequent catalyst zones.

The first region of the inert zone of the preliminary zone advantageously takes up from 5 to 25 cm, preferably from 10 to 20 cm. The second region of the catalyst material bed of the preliminary zone advantageously takes up from 10 to 75 cm, preferably from 30 to 50 cm. Accordingly, the first region of the inert zone of the preliminary zone advantageously takes up from 5 to 70%, preferably from 15 to 40%, of the total preliminary zone. The second region of the catalyst material bed of the preliminary zone therefore advantageously takes up from 30 to 95%, preferably from 60 to 85%, of the total preliminary zone. The activity of the preceding catalyst zone advantageously corresponds to the activity of the first subsequent catalyst zone.

Apart from the preliminary zone, it is possible to use, if appropriate, further inert and/or catalyst material to equalize the pressure drop over the individual tubes of the shell-and-tube reactor.

The process of the invention is particularly suitable for the gas-phase oxidation of aromatic $C_6$-$C_{10}$-hydrocarbons such as benzene, the xylenes, toluene, naphthalene or durene (1,2,4,5-tetramethylbenzene) to carboxylic acids and/or carboxylic anhydrides such as maleic anhydride, phthalic anhydride, benzoic acid and/or pyromellitic dianhydride. The process is particularly useful for preparing phthalic anhydride from o-xylene and/or naphthalene.

The way in which the process of the invention is carried out is known to those skilled in the art and is described, for example, in WO 2004/103561 on pages 6 and 7.

The process of the invention brings about rapid heating of the reaction gas at the beginning of the catalyst bed.

In contrast to WO 2006/92305, WO 2006/92304 and the European patent application number 06112510.0, in the present invention the reaction gas is likewise heated below the salt bath temperature but there is no increased safety risk if the gas temperature in the preliminary zone should exceed the salt bath temperature.

The present invention further provides a catalyst system for carrying out gas-phase oxidation processes, in which a gaseous stream comprising at least one aromatic hydrocarbon and molecular oxygen, with the proviso that the catalyst system comprises at least two catalyst zones arranged in series in the flow direction of the gaseous stream and the activities of the catalysts in adjoining catalyst zones are different from one another, with the proviso that a catalyst and/or inert zone precedes the adjoining catalyst zones in a direction opposite to the flow direction of the gas, with the product of diameter times height of the preceding inert and/or catalyst rings being smaller than at least one of the subsequent catalyst zones or the volume of the preceding inert and/or catalyst rings being smaller than at least one of the subsequent catalyst zones or the ratio of surface area to volume of the preceding inert and/or catalyst rings being greater than at least one of the subsequent catalyst zones.

The present invention makes available a catalyst system whose initial hot spot is very close to the reactor inlet. The greater utilization of the catalyst bed toward the reactor inlet makes it possible to achieve longer operating lives. Furthermore, the abovementioned undesirable secondary reactions caused by migration of the hot spot into more active catalyst zones occurs only at a later point in time than in the case of catalyst systems of the prior art.

The invention is illustrated by the accompanying FIGS. 1a and 1b and the following examples.

EXAMPLES

Catalyst 1: as described in U.S. Pat. No. 6,586,361, Example 9 (i.e. "catalyst IIe"), series 8, having a geometry of 8×6×5 mm (external diameter×height×internal diameter)

Catalyst 2: as described in U.S. Pat. No. 6,586,361, Example 10 (i.e. "catalyst III"), series 8, having a geometry of 8×6×5 mm (external diameter×height×internal diameter)

Preliminary Zones:

Preliminary zone 1: inert steatite rings having a geometry of 5×3×2 mm (external diameter×height×internal diameter)

Preliminary zone 2: inert steatite rings having a geometry of 7×7×4 mm (external diameter×height×internal diameter) having notches having a cut of 1.5 mm×1.5 mm on each end face as shown in FIG. 1a Preliminary zone 3: 10.1% of active composition on steatite rings, with the composition corresponding to that of catalyst 1, having a geometry of 7×7×4 mm (external diameter×height×internal diameter)

Preliminary zone 4: inert steatite rings having a geometry of 8×6×5 mm (external diameter×height×internal diameter)

Catalyst System Test:

Test 1: according to the invention, catalyst system in flow direction: 10 cm of preliminary zone 1, 170 cm of catalyst 1, 130 cm of catalyst 2

Test 2: according to the invention, catalyst system in flow direction: 10 cm of preliminary zone 2, 170 cm of catalyst 1, 130 cm of catalyst 2

Test 3: according to the invention, catalyst system in flow direction: 10 cm of preliminary zone 2, 40 cm of preliminary zone 3, 170 cm of catalyst 1, 130 cm of catalyst 2

Test 4: not according to the invention, catalyst system in flow direction: 10 cm of preliminary zone 4, 170 cm of catalyst 1, 130 cm of catalyst 2

Procedure for the Catalyst System Tests:

The four catalyst systems were tested at a loading of 70 g/standard m³ of o-xylene. At the same salt bath temperature of 355° C., the hot spot positions shown in Table 1 were measured.

TABLE 1

| Test | Hot Spot Position [cm] |
|---|---|
| 1 | 65 |
| 2 | 80 |
| 3 | 75 |
| 4 | 90 |

The invention claimed is:

1. A process for gas-phase oxidation which comprises passing a gaseous stream comprising at least one aromatic hydrocarbon and molecular oxygen through at least two catalyst zones containing rings and arranged in series in the flow direction of the gaseous stream and the activities of the catalysts in adjoining catalyst zones are different from one another, wherein a catalyst zone precedes the adjoining catalyst zones in a direction opposite to the flow direction of the gas, and at least one of the following parameters exists:
   a. with the product of diameter times height of the catalyst rings in the preceding zone being smaller than in at least one of the subsequent catalyst zones, or
   b. the volume of the catalyst rings in the preceding zone being smaller than in at least one of the subsequent catalyst zones or
   c. the ratio of surface area to volume of the catalyst rings in the preceding zone being greater than in at least one of the subsequent catalyst zones.

2. The process according to claim 1, wherein
   a) the product of diameter times height of the catalyst rings in the preceding zone is at least 5-10% less than in at least one of the subsequent catalyst zones, or
   b) the volume of the catalyst rings in the preceding zone is at least 5-10% smaller than in at least one of the subsequent catalyst zones or
   c) the ratio of surface area to volume of the catalyst rings in the preceding zone is at least 5-10% greater than in at least one of the subsequent catalyst zones.

3. The process according to claim 1, wherein
a) the product of diameter times height of the catalyst rings in the preceding zone is less than or equal to 45 mm², or
b) the volume of the catalysts rings in the preceding zone is less than or equal to 170 mm³ or
c) the ratio of surface area to volume of the catalyst rings in the preceding zone is greater than or equal to 180 mm⁻¹.

4. The process according to claim 1, wherein the volume is reduced by means of notches on each end face of the rings.

5. The process according to claim 1, wherein the bed length of the preceding catalyst zone is from 2.5 to 20% of the total bed length.

6. The process according to claim 1, wherein the preceding catalyst zone has no activity or the activity of the first subsequent catalyst zone.

7. The process according to claim 1, wherein the preceding catalyst zone comprises a region composed of an inert material and a region composed of catalyst material, with the region composed of inert material being closest to the gas inlet.

8. The process according to claim 7, wherein the inert material region makes up from 15 to 40% of the total length of the preliminary zone.

9. The process according to claim 1, wherein phthalic anhydride is prepared from o-xylene and/or naphthalene.

10. The process according to claim 1, wherein the initial hot spot is very close to a reactor inlet.

11. The process according to claim 1, wherein the product of diameter times height of the catalyst rings in the preceding zone is less than or equal to 45 mm².

12. The process according to claim 1, wherein the volume of the catalysts rings in the preceding zone is less than or equal to 170 mm³.

13. The process according to claim 1, wherein the ratio of surface area to volume of the catalyst rings in the preceding zone is greater than or equal to 180 mm⁻¹.

14. The process according to claim 1, wherein the product of diameter times height of the catalyst ring in the preceding zone being smaller than in at least one of the subsequent catalyst zones.

15. The process according to claim 1, wherein the volume of the catalyst rings in the preceding zone being smaller than in at least one of the subsequent catalyst zones.

16. The process according to claim 1, wherein the ratio of surface area to volume of the catalyst rings in the preceding zone being greater than in at least one of the subsequent catalyst zones.

17. A process for gas-phase oxidation which comprises passing a gaseous stream comprising at least one aromatic hydrocarbon and molecular oxygen through at least two catalyst zones containing rings and arranged in series in the flow direction of the gaseous stream and the activities of the catalysts in adjoining catalyst zones are different from one another, wherein an inert zone precedes the adjoining catalyst zones in a direction opposite to the flow direction of the gas, and at one of the following parameters exists
a. with the product of diameter times height of the inert rings in the preceding zone being smaller than in at least one of the subsequent catalyst zones,
b. the volume of the preceding rings in the preceding zone being smaller than in at least one of the subsequent catalyst zones or
c. the ratio of surface area to volume of the inert rings in the preceding zone being greater than in at least one of the subsequent catalyst zones.

18. The process according to claim 17, wherein the product of diameter times height of the inert rings in the preceding zone being smaller than in at least one of the subsequent catalyst zones.

19. The process according to claim 17, wherein the volume of the inert rings in the preceding zone being smaller than in at least one of the subsequent catalyst zones.

20. The process according to claim 17, wherein the ratio of surface area to volume of the inert rings in the preceding zone being greater than in at least one of the subsequent catalyst zones.

21. The process according to claim 1, wherein there are 3 to 5 catalyst zones.

22. The process according to claim 1, wherein there are 3 catalyst zones.

23. The process according to claim 1, wherein there are 4 catalyst zones.

\* \* \* \* \*